(12) United States Patent
Geipel et al.

(10) Patent No.: US 9,283,319 B2
(45) Date of Patent: Mar. 15, 2016

(54) CANNULA ASSEMBLIES AND AMBULATORY INFUSION SYSTEMS WITH PRESSURE SENSORS MADE OF STACKED COPLANAR LAYERS

(71) Applicant: Roche Diagnostics International AG, Rotkreuz (CH)

(72) Inventors: Andreas Geipel, Oftringen (CH); Florian Kuhni, Wabern (CH); Christoph Huwiler, Baar (CH); Ulrich Haueter, Grosshochstetten (CH)

(73) Assignee: ROCHE DIAGNOSTICS INTERNATIONAL AG, Rotkreuz (CH)

( * ) Notice: Subject to any disclaimer, the term of this patent is extended or adjusted under 35 U.S.C. 154(b) by 295 days.

(21) Appl. No.: 13/656,070

(22) Filed: Oct. 19, 2012

(65) Prior Publication Data

US 2013/0042693 A1 Feb. 21, 2013

Related U.S. Application Data

(62) Division of application No. 12/725,819, filed on Mar. 17, 2010, now Pat. No. 8,313,468.

(30) Foreign Application Priority Data

Mar. 17, 2009 (EP) ..................... 09003798

(51) Int. Cl.
*A61M 5/162* (2006.01)
*G01L 9/12* (2006.01)
(Continued)

(52) U.S. Cl.
CPC ........... *A61M 5/158* (2013.01); *A61M 5/16854* (2013.01); *G01L 9/0005* (2013.01);
(Continued)

(58) Field of Classification Search
CPC ... G01L 9/0005; G01L 9/0041; G01L 9/0042; G01L 9/1072; A61M 2205/0244; A61M 2205/33; A61M 2205/3331; A61M 5/158; A61M 5/16854
USPC ................ 604/65–67, 151; 73/723–724, 713, 73/714.18, 204.26, 862.626, 861.47, 718; 361/209–291

See application file for complete search history.

(56) References Cited

U.S. PATENT DOCUMENTS

| 4,064,550 A | 12/1977 | Dias et al. |
| 4,204,244 A | 5/1980 | Ho |

(Continued)

FOREIGN PATENT DOCUMENTS

| EP | 0 009 313 A1 | 8/1979 |
| EP | 1 207 378 A1 | 8/1999 |

(Continued)

OTHER PUBLICATIONS

European Search Report for Application EP09003798.7 dated Dec. 23, 2009.

*Primary Examiner* — Quynh-Nhu H Vu
(74) *Attorney, Agent, or Firm* — Dinsmore & Shohl LLP

(57) ABSTRACT

Cannula assemblies with pressure sensors made of stacked coplanar layers and ambulatory infusion systems comprising the same are disclosed. The cannula assemblies include a hub and an infusion cannula. The hub includes a pressure sensor and a fluid channel fluidly coupled to the infusion cannula. The pressure sensor is formed from a stack of coplanar layers including a top layer, a base layer an electrode layer and a counter electrode layer. The fluid channel is positioned between the top layer and the base layer. The electrode layer is positioned between the top layer and the base layer and coupled to the fluid channel. The counter-electrode layer is positioned between the top layer and the electrode layer. A spacer layer having a through cut-out defining an electrode cavity is disposed between the top layer and the base layer such that the electrode layer extends across the electrode cavity.

12 Claims, 8 Drawing Sheets

(51) Int. Cl.
*A61M 5/158* (2006.01)
*A61M 5/168* (2006.01)
*G01L 9/00* (2006.01)

(52) U.S. Cl.
CPC ...... *G01L9/0041* (2013.01); *A61M 2205/0244* (2013.01); *A61M 2205/33* (2013.01); *A61M 2205/3331* (2013.01)

(56) References Cited

U.S. PATENT DOCUMENTS

| | | | |
|---|---|---|---|
| 4,380,041 A | 4/1983 | Ho | |
| 4,741,214 A * | 5/1988 | Vidmantas | 73/708 |
| 5,034,848 A | 7/1991 | Rowlette et al. | |
| 5,050,034 A * | 9/1991 | Hegner et al. | 361/283.4 |
| 5,186,054 A | 2/1993 | Sekimura | |
| 5,719,740 A * | 2/1998 | Hayashi et al. | 361/283.4 |
| 6,032,536 A | 3/2000 | Peeters et al. | |
| 6,597,560 B2 | 7/2003 | Potter | |
| 6,830,558 B2 * | 12/2004 | Flaherty et al. | 604/67 |
| 6,904,808 B2 | 6/2005 | Masuda | |
| 6,928,879 B2 | 8/2005 | Partridge et al. | |
| 2002/0115920 A1 | 8/2002 | Rich et al. | |
| 2003/0200812 A1 | 10/2003 | Kuhn et al. | |
| 2007/0261496 A1 | 11/2007 | Jonsson et al. | |
| 2008/0200897 A1 | 8/2008 | Hoss et al. | |

FOREIGN PATENT DOCUMENTS

| | | |
|---|---|---|
| EP | 1 961 436 A1 | 2/2007 |
| WO | 2005/077262 A1 | 8/2008 |

* cited by examiner

CANNULA ASSEMBLIES AND AMBULATORY INFUSION SYSTEMS WITH PRESSURE SENSORS MADE OF STACKED COPLANAR LAYERS

CROSS REFERENCE TO RELATED APPLICATIONS

This application is a divisional of U.S. patent application Ser. No. 12/725,819 filed Mar. 17, 2010 which claims priority to European patent application number EP 09003798 filed Mar. 17, 2009, the entirety of which is herein incorporated by reference.

TECHNICAL FIELD

The present specification is directed to cannula assemblies for ambulatory drug infusion over extended time periods comprising pressure sensors made from stacks of coplanar layers and ambulatory infusion systems comprising such pressure sensors.

BACKGROUND

Ambulatory infusion systems and devices for the infusion of a liquid drug over an extended time period are known in the art for a number of therapies. In particular, such devices form the basis for a state-of-the-art therapy for Diabetes Mellitus by CSII (Continuous Subcutaneous Insulin Infusion). A suitable device is disclosed, for example, in WO2003053498A2 to which reference is made for the general design and features of such devices.

Besides diabetes therapy, such infusion devices may be used for a number of other therapies, such as cancer treatment or pain therapy, without substantial modification. The following description mainly refers to CSII therapy as an example of one specific application. However, it should be understood that the embodiments described herein are not limited to this specific therapeutic application.

When using an ambulatory infusion device a number of error situations or hazardous situations may occur such as occlusions of the infusion cannula or the infusion tubing. Accordingly, it is desirable to detect such situations as early as possible. For this purpose, the fluidic pressure of the drug may be continuously monitored. In state-of-the-art devices this is typically done by measuring the reaction-force exerted by a plunger of the drive system of the infusion device on a plug of the drug cartridge. Corresponding designs are disclosed in U.S. Pat. No. 6,362,591, among others. This approach, however, involves a complex and critical electromechanical design of the infusion system, substantially adds to the size of the device and involves a number of measuring uncertainties due to friction. It is therefore favorable to directly measure the fluidic pressure of the drug. Pressure measurement arrangements such as those described in WO 2007/093064 have been designed for this purpose. Those arrangements, however, involve complex and expensive disposable components. Furthermore, it would be favorable to measure the drug pressure directly at the infusion cannula rather than at the pump outlet.

U.S. Pat. No. 6,830,558 B2 discloses a flow condition sensor assembly for an infusion device with a first electrode which is secured on a diaphragm and a second electrode which is positioned in a fixed location with respect to the first electrode. An impedance meter is connected to the electrodes. The diaphragm is resilient and may flex into a curved sensor chamber, thus modifying the impedance which may be measured between the first electrode and the second electrode. However, the sensor comprises complex components and must be carefully assembled.

SUMMARY

In one embodiment, a cannula assembly includes a hub and an infusion cannula. The hub includes a pressure sensor and a fluid channel fluidly coupled to the infusion cannula. The pressure sensor includes a stack of coplanar layers including a top layer, a base layer, an electrode layer and a counter electrode layer. At least a portion of the fluid channel is positioned between the top layer and the base layer. The electrode layer is positioned between the top layer and the base layer and is flexibly coupled to the fluid channel. The counter-electrode layer is positioned between the top layer and the electrode layer. The counter electrode-layer and the electrode layer form the electrodes of a sensing capacitor. A first spacer layer having a through cut-out defining an electrode cavity is disposed between the top layer and the base layer such that the electrode layer extends across the electrode cavity. A positive fluidic pressure in the fluid channel flexes the electrode layer into the electrode cavity thereby modifying the capacitance of the sensing capacitor.

In another embodiment, an ambulatory infusion system for the infusion of a liquid drug into a patient's body over an extended time period includes a drug container and an infusion cannula fluidically coupled to the drug container. An infusion device is fluidly coupled to the drug container. A pressure sensor is electrically coupled to a measuring unit and fluidically coupled to the drug container and the infusion cannula with a fluid channel. The pressure sensor includes a stack of coplanar layers including a top layer, a base layer, an electrode layer and a counter electrode layer. At least a portion of the fluid channel is positioned between the top layer and the base layer. The electrode layer is positioned between the top layer and the base layer and is flexibly coupled to the fluid channel. The counter-electrode layer is positioned between the top layer and the electrode layer. The counter electrode-layer and the electrode layer form the electrodes of a sensing capacitor. A first spacer layer having a through cut-out defining an electrode cavity is disposed between the top layer and the base layer such that the electrode layer extends across the electrode cavity. A positive fluidic pressure in the fluid channel flexes the electrode layer into the electrode cavity thereby modifying the capacitance of the sensing capacitor.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIG. 8b schematically depicts a bottom view of the pressure sensor of FIG. 8a;

FIG. 12b schematically depicts a corresponding bottom view of the pressure sensor of FIG. 12a.

DETAILED DESCRIPTION

One embodiment described herein is directed towards a cannula assembly, comprising an infusion cannula and a hub. The hub comprises a pressure sensor with a fluid channel fluidically arranged upstream of the infusion cannula. The pressure sensor comprises a stack of coplanar layers with a rigid top layer and a rigid base layer, a resilient metallic electrode layer and a metallic counter electrode layer. The electrode layer and the counter-electrode layer are electrodes of a sensing capacitor and are separated by a first spacer layer which has a through cut-out defining an electrode cavity. The fluid channel is coupled to the electrode layer such that a fluidic positive pressure of the drug in the fluid channel causes the electrode layer to flex into the electrode cavity, thus modifying the capacitance of the sensing capacitor.

The hub is the extracorporeal portion of the cannula assembly from which the infusion cannula projects. It is typically designed to be attached to the patient's body or skin, for example with a belt or an adhesive layer contacting the skin. The infusion cannula may be directly connected to the fluid channel and integral with the drug outlet. The cannula may be of any design known in the art and may be made of metal, such as medical grade stainless steel, or a plastic material, such as Teflon. The hub may be designed such that the cannula is placed into the skin substantially perpendicular to the skin or at an angle of less than 90°, e.g., 10° to 20°, relative to the skin.

In some embodiments, the cannula assembly comprises a fluidic coupler upstream of the pressure sensor and in fluid communication with the fluid channel. The fluidic coupler is configured to couple the cannula assembly to an infusion device. The fluidic coupler may be a releasable coupler, such as a Luer coupler or another type of coupler. The coupler may alternatively be designed such that the fluidic connection may be established by the patient but may not be released again, for example by providing snapping elements, or the like.

Alternatively, the cannula assembly may not comprise a dedicated coupler but may be provided with further components, such as a drug cartridge or a dosing unit readily attached.

The cannula assembly may be designed for direct coupling to an infusion device or for coupling via additional tubing.

Figure 5:
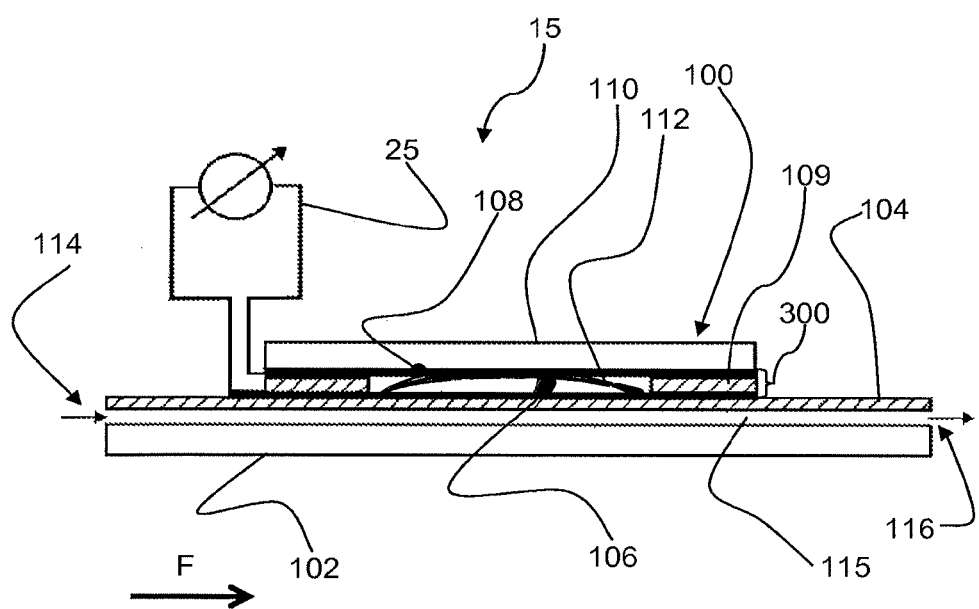
FIG. 5, FIG. 6, and FIG. 7 schematically depict stacks of coplanar layers of exemplary pressure sensors according to one or more embodiments shown and described herein.

The coplanar design of the layers of the pressure sensor provides a flat, sandwich-like structure which is well-suited for large-scale manufacture. The layers forming the stack may be bonded to each other using established technologies such as laminating, adhesive bonding, ultrasonic welding or laser bonding. In advantageous embodiments, the inner layers of the pressure sensor, i.e., the layers which are arranged between the top layer and the base layer, in particular the electrode layer, the counter-electrode layer and the first spacer layer, are of substantially the same size, thus simplifying the positioning during manufacture. In FIG. 5, an example embodiment is shown wherein the electrode layer 106, the counter-electrode layer 108, and the first-spacer layer 109 prior to the through cut-out which forms the electrode cavity 112, are of substantially the same length. The surface areas of the electrode layer and the counter-electrode layer are larger than the area of the electrode cavity, such that the electrode cavity is covered by the electrode layer and the counter-electrode layer over its entire area.

The inner layers have a uniform thickness over their entire surface area resulting in the surfaces being coplanar without recesses or the like. This is also true for the inner surfaces of the top layer and the base layer which contact the inner layers. This design allows the single layers to be thin and simplifies the positioning and bonding of the layers. In some embodiments, the outer surfaces of the top layer and the base layer, respectively, are coplanar with the surfaces of the inner layers, such that all layers of the stack are coplanar.

While large dimensions and surface areas of the layers simplify manufacture and increase the capacitance of the sensing capacitor, smaller dimensions facilitate a compact design. In an infusion system for CSII, the size of the electrode cavity may be from about 15 mm$^2$ to about 80 mm$^2$. The electrode cavity and the fluid cavity may generally have any suitable shape according to the overall design requirements. For example, the shape of the electrode cavity may be circular, elliptical rectangular shape or any other suitable shape.

The resulting nominal capacitance of the sensing capacitor is smaller than 30 pF and may be in the range of 3 pF to 5 pF. Other nominal capacitances, however, are also possible. The term 'nominal capacitance' refers to the capacitance of the sensing capacitor in the unloaded state of the pressure sensor, that is, if no pressure is acting on the electrode layer which would cause the electrode layer to flex. The sensing capacitor is defined by the surface of the electrode layer and the counter-electrode as well as the volume between those layers.

In one embodiment the fluid channel is widens to form a fluid cavity of at least the same size and in alignment with the electrode cavity such that the fluidic pressure of the drug in the fluid channel acts equally on the entire surface electrode layer in the area (i.e., the area which covers the through cut-out in the first spacer layer) which may bent under the influence of a fluidic drug pressure. The fluid channel may be formed in the base layer during injection-molding of the base layer or may be formed by punching, milling, or any another suitable forming process.

Alternatively, a foil layer may be provided with embedded fluid channels and/or cavities. Those channels and cavities may be formed by hot embossing or deep drawing.

In one embodiment, the fluid channel is arranged inside the coplanar stack of layers which is bounded by the top layer and the base layer. In one embodiment the fluid channel may be separated from the electrode layer by an electrode sealing layer which is attached to the electrode layer. The electrode sealing layer is resilient in order to allow it to flex together with the electrode layer.

The pressure which causes the electrode layer to flex is the differential pressure between the drug pressure in the fluid channel and the reference pressure in the electrode cavity. A fluidic drug pressure that is larger than the reference pressure is referred to as a 'positive pressure' and a fluidic drug pressure that is smaller than the reference pressure is referred to as a 'negative pressure'. If the electrode cavity is vented to the environment, the electrode cavity is filled with air and the reference pressure is the environmental pressure. Alternatively, the electrode cavity may be hermetically sealed and filled with air or another fluid, typically a gas, during manufacture. In this case, the reference pressure is the constant pressure of this gas.

In some embodiments, foils are used at least for the electrode layer and the first spacer layer. In these embodiments the electrode layer is a metal foil or a compound of a metal foil and a non-metal carrier foil or is made by metalizing a non-metal carrier foil, for example by chemical metallization, galvanic metallization or lacquering.

Foils are particularly well suited for use as the electrode layer and the first spacer layer due to their inherent elastic and/or resilient properties and general ease of manufacture. The foils may be supplied on spools or in sheets which allows fast parallel and/or serial processing. Different mechanical properties, such as different rigidities, may be achieved by appropriate selection of the foil materials as well as the thickness.

In one embodiment metalized foils are used which are substantially unstructured and covered with metal over their entire surface, thus avoiding critical structuring steps, such as partial etching, partial metallization, or the like. Therefore, large-scale manufacture may be carried out in an economic and cost-efficient manner. The sensors may be assembled by stacking and attaching the foil layers as supplied from spools or as sheets. Subsequently, the foil sandwich may be cut or punched, as known in the art, in order to separate individual sensors.

In one embodiment, a first spacer layer is provided as this allows the manufacture of the through cut-out by cutting or punching. Those steps may be performed simultaneously for a large number of sensors in one step, prior to bonding the foil to other foils and prior to separating the individual sensors as described above. The first spacer layer may be more rigid than the electrode layer such that the first spacer layer is substantially stiff during operation and/or handling.

The other layers of the stack may also be made from foils. Alternatively, some layers, in particular the top layer and the base layer, are made of plastic and may be injection molded parts. In such an embodiment, the top-layer and/or the base layer may be integral with the hub housing and form a supporting structure or frame inside which the other layers are arranged. The counter-electrode layer may be made by a metal foil or metalized foil like the electrode layer, or may be made by metallization of the top layer. For the layers made of foils, a variety of known materials may be used, for example polymeric materials such as PMMA, PC, PSU, or PEEK. A typical advantageous range for the foil thickness is from about 50 microns to about 200 microns.

In some embodiments, the first spacer layer is arranged between and in contact with the electrode layer and the counter-electrode layer.

In some of those embodiments, the electrode layer, the counter-electrode layer and the electrode cavity are designed such that, upon reaching a maximum threshold pressure, the electrode layer touches the counter-electrode layer. Factors that may be adjusted to facilitate this embodiment are the shape and dimensions of the electrode cavity as well as the rigidity of the electrode layer and the electrode sealing layer. Under the given dimensional restrictions, those parameters may be adjusted for a given maximum threshold pressure by routine computational and/or experimental work.

The design of the sensing capacitor may be such that the electrode layer and the counter-electrode layer establish a galvanic contact with the electrode layer touching the counter-electrode layer at the maximum threshold pressure. This galvanic contact may be detected in order to trigger an occlusion or overpressure alarm.

Alternatively, at least one of the electrode layer and the counter-electrode layer comprises an insulation layer which faces the other of the electrode layer or the counter-electrode layer, thus preventing a galvanic contact from being established between the electrode layer and the counter-electrode layer. In this case, the capacitance of the sensing capacitor is saturated when the electrode layer and the counter-electrode layer touch each other at the maximum threshold pressure.

In one embodiment the fluid channel of the pressure sensor may comprise a flow restrictor. Such a flow restrictor may be arranged downstream of the electrode cavity. If a drug is administered, the flow restrictor increases the fluidic pressure upstream of the flow resistor according to the law of Hagen-Poiseuille. Due to the increased pressure, the electrode layer flexes which, in turn, changes the capacitance. The flow restrictor may be used to increase the length of the fluid path downstream of the fluid cavity and/or reduce the hydraulic diameter downstream of the fluid cavity. Where the flow restrictor is used to increase the length of the fluid path downstream of the fluid cavity, the fluid channel may have a serpentine-shaped portion.

In another embodiment the pressure sensor may comprise a reference capacitor in addition to the sensing capacitor. The reference capacitor comprises a reference electrode layer and a reference counter-electrode layer. Providing a reference capacitor which is vented to the environment permits the signal provided by the sensing capacitor to be adjusted to compensate for undesired environmental effects such as changing temperature and atmospheric pressure. In one embodiment, the reference capacitor is of the same design as the sensing capacitor. In another embodiment the reference capacitor has the same or a similar nominal capacitance as the sensing capacitor and comprises a reference pressure cavity which is vented to the environment via a reference venting aperture such that the environmental pressure acts on and flexes the reference electrode layer. Any change in the environmental conditions will accordingly act on the sensing capacitor and the reference capacitor in the same way.

In the embodiments which include a reference capacitor, the sensing capacitor and the reference capacitor are arranged next to each other in the same plane. Alternatively, the sensing capacitor and the reference capacitor may be arranged in a stack, thus reducing the surface area of the stack while increasing its thickness.

In some embodiments comprising a reference capacitor, either the electrode layer and the reference electrode layer or the counter-electrode layer and the reference counter-electrode layer are formed in a single common layer, thus forming a common electrode.

In some embodiments, only the electrode layer flexes under the influence of the fluidic pressure of the drug, while the counter-electrode layer maintains its planar shape. Alternatively, the fluid channel may be coupled to the counter-electrode layer such that a fluidic pressure of the drug in the fluid channel results in the counter-electrode layer being flexed with the electrode layer thus modifying the capacitance of the sensing capacitor. This measure increases the capacitance variation resulting from a fluidic pressure variation, and, thus, the sensitivity of the pressure sensor.

The electrode layer, the counter-electrode layer and the fluid channel may be arranged such that the capacitance of the sensing capacitor increases upon increasing fluidic pressure of the drug in the fluid channel. Alternatively, the arrangement may be such that the capacitance of the sensing capacitor decreases with increasing fluidic pressure of the drug in the fluid channel. Further details of both embodiments are discussed below in exemplary embodiments.

In some embodiments, the pressure sensor comprises an secondary sensing capacitor, the secondary sensing capacitor comprising a secondary electrode layer and a secondary counter-electrode layer, the secondary electrode layer, the secondary counter-electrode layer and the fluid channel being arranged such that the pressure in the fluid channel modifies the capacitance of the sensing capacitor and the capacitance of the secondary sensing capacitor in opposite ways (i.e., the capacitance of one is decreased while the capacitance of the other is increased).

The sensing capacitor and the secondary sensing capacitor of such an embodiment are advantageously designed in similar manner. Both capacitors comprise a stack of coplanar layers, wherein some of the layers may be common to both the pressure sensor and the secondary pressure sensor. This embodiment facilitates improved sensitivity as well as the compensating for environmental effects, since the fluidic drug pressure in the flow channel modifies the capacitances of the sensing capacitor and the secondary sensing capacitor in opposite ways, while environmental effects act on both capacitors in the same way. The geometric arrangement of the sensing capacitor and the secondary sensing capacitor may be next to each other or may be stacked.

In another embodiment, an ambulatory infusion system for the infusion of a liquid drug into a patient's body over an extended time period, the ambulatory infusion system comprising a drug container and an infusion cannula fluidically coupled to the drug container. The infusion cannula may be placed into the patient's subcutaneous tissue for drug infusion. An infusion device is coupled to the drug container for controlled drug administration via the infusion cannula. A pressure sensor with a fluid channel is coupled to the drug container and the infusion cannula. The pressure sensor includes a sensing capacitor. A measuring unit is coupled to the pressure sensor and is programmed to evaluate variations of the capacitance of the sensing capacitor. The pressure sensor comprises a stack of coplanar layers with a rigid top layer and a rigid base layer, a resilient metallic electrode layer and a metallic counter electrode layer. The electrode layer and the counter-electrode layer are electrodes of a sensing capacitor and are separated by a first spacer layer which has a through cut-out defining an electrode cavity. The fluid channel is coupled to the electrode layer such that a fluidic positive pressure of the drug in the fluid channel causes the electrode layer to flex into the electrode cavity, thus modifying the capacitance of the sensing capacitor.

The overall architecture of the infusion device may follow the design disclosed in WO2003/053498A2, for example. The infusion device may be a computer-controlled syringe-driver pump but may alternatively be of a different type and comprise, for example, a micro membrane pump or a dosing unit as disclosed in EP1970677A1.

The measuring unit may comprise a capacitance measurement circuit. For this purpose, the measuring unit may include filters, amplifiers, reference voltage and/or reference current supplies, analogue-to-digital converters, and the like. The capacitance measurement circuit may be based on a capacitance-to-voltage converter such as the integrated circuit CAV424 available from Analog Microelectronics GmbH, Germany. If the pressure sensor comprises a sensing capacitor and a secondary sensing capacitor, the measuring circuit may be designed to measure the capacitance of both the sensing capacitor and the secondary sensing capacitor. The measuring unit may further detect the presence of a galvanic contact between the electrode and the counter-electrode.

The pressure sensor may be included in the main housing of the infusion device. This is the case if the whole system is disposable. Alternatively, the pressure sensor may be included in a disposable component, such as the drug container. In another embodiment, the pressure sensor is included in an adapter which is coupled to the drug container and is coupled to an infusion tubing. In another embodiment, the drug sensor is included in a cannula assembly as described above.

The measuring unit and/or a controller of the infusion device are configured to generate a warning or an alarm in case the fluidic pressure or a variation of the fluidic pressure indicates the occurrence of an error condition, such as an occlusion.

Whereas the position of the pressure sensor in the infusion device may differ from the position of the pressure sensor as disclosed above in the context of a cannula assembly, all embodiments of the pressure sensor described above may also be embodiments of a pressure sensor in an ambulatory infusion system.

Referring now to FIG. 1-FIG. 12b, FIG. 1 schematically depicts the overall architecture of one embodiment of an ambulatory infusion system. The infusion system comprises an infusion device 5, an infusion tubing 10, a pressure sensor 15 with a sensing capacitor 16 and an optional flow restrictor 17, and an infusion cannula 20 which is designed to be placed into the patient's subcutaneous tissue for drug infusion.

In this embodiment, the infusion system further comprises a measuring unit 25 which operatively couples the pressure sensor 15 to a controller of the infusion device 5. While shown as a separate unit, the measuring unit 25 may be fully or partially integral with the infusion device 5. The measuring unit 25 may include circuitry, including a processor, memory, and related circuit components, programmed with an executable instruction set for processing and evaluating electrical signals generated by the pressure sensor 15. The measuring unit 25 is programmed to detect the presence of a substantially continuous pressure increase over time resulting from an occlusion in the fluidic system, such as an inclusion in the infusion cannula 20. The measuring unit 25 may additionally or alternatively be programmed to control the drug administration by the infusion device 5 by detecting the presence of short pressure pulses which accompany the administration of each drug pulse through the system. The infusion device 5 may be designed for basal drug administration by administering small drug pulses every few minutes, as is the case in typical syringe-driver pumps. Each of these drug pulses is associated with a pressure peak which may be detected by the pressure sensor 15 and the presence of which may be determined by the measuring unit 25. The substantially continuous administration of larger drug amounts, such as the administration of drug boli, are associated with a substantially constant pressure plateau during the administration which also may be determined by the measuring unit 25.

FIG. 2a graphically depicts an exemplary administration volume curve 400 and FIG. 2b graphically depicts a pressure curve 420 corresponding to the volume curve of FIG. 2a as measured by the pressure sensor 15 as a function of time t. The infusion system administers small basal drug pulses 402 in equidistant time intervals resulting in a quasi-continuous basal administration. Each basal drug pulse 402 is reflected by a corresponding basal pressure pulse 422. At time $t_1$ an additional on-demand bolus 404 with a larger volume is administered. The corresponding temporary bolus pressure increase 424 may be a short pulse or may have a plateau as shown in the example in FIG. 2a, depending on the administration regime and the time required for the administration. At some point between $t_2$ and $t_3$ an occlusion is established, that is, the fluid path is blocked. Subsequent basal administrations result in a stepwise pressure increase, with a step 426 occurring each time a basal drug pulse 402 is administered. Between the steps 426, the pressure may stay substantially constant or slightly decrease due to the elasticity of the fluidic system. The administration of a drug bolus would result in an even steeper pressure increase (not shown).

Figure 3:
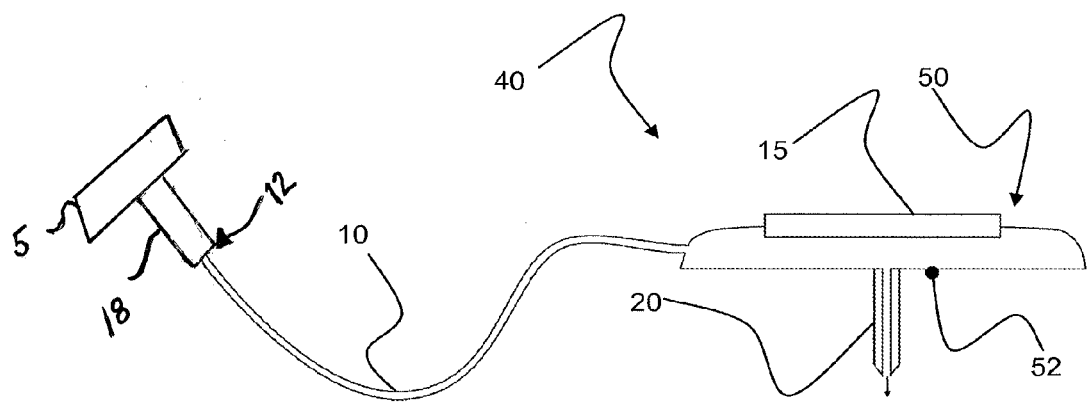
FIG. 3 and FIG. 4 schematically depict exemplary cannula assemblies according to one or more embodiments shown and described herein.
Figure 2:
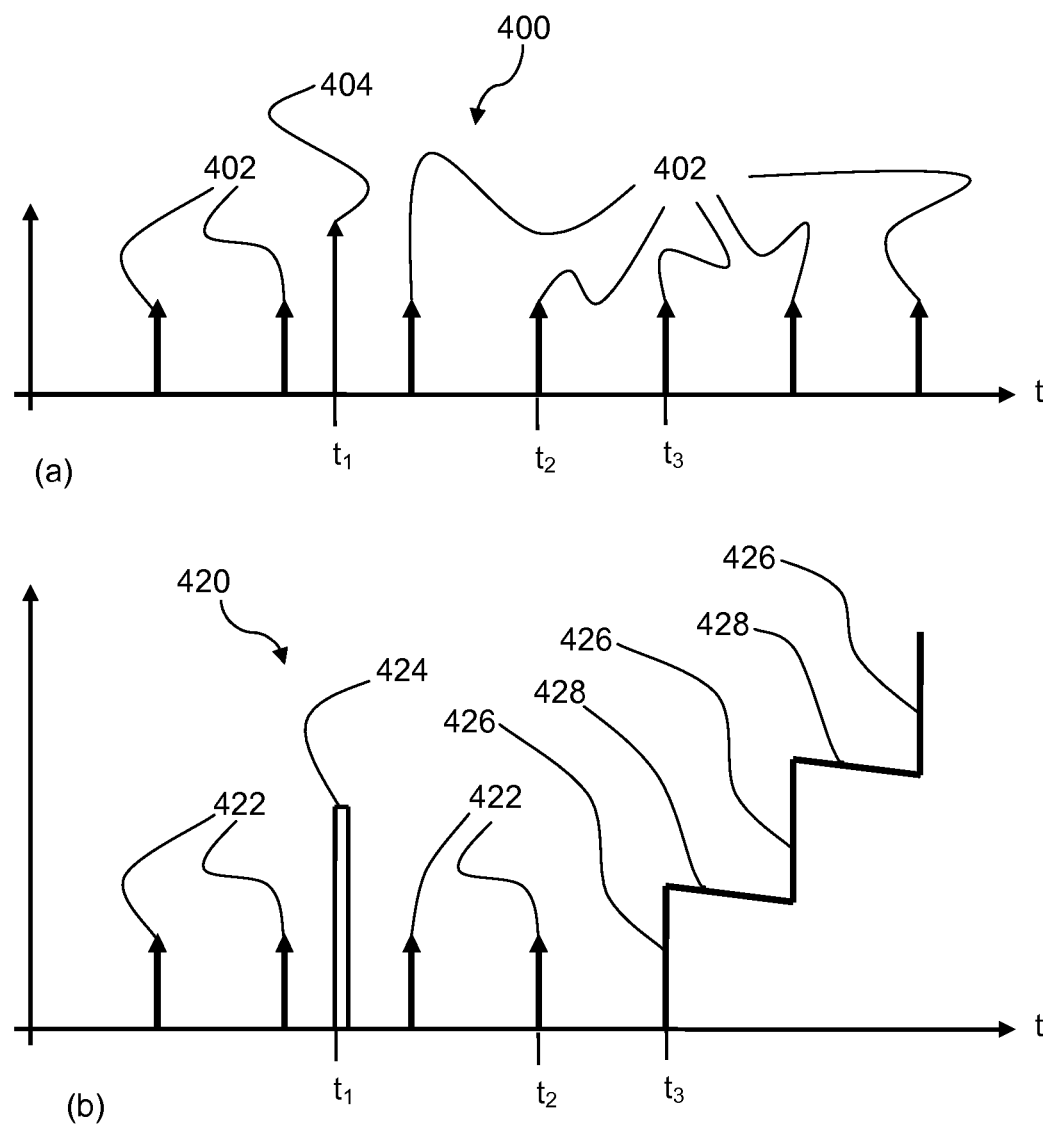
FIGS. 2a and 2b graphically depict a drug volume curve and a corresponding pressure curve of an infusion system according to one ore more embodiments shown and described herein.

FIG. 3 schematically depicts one embodiment of an exemplary cannula assembly 40. The pressure sensor 15 is integrated into the extra-corporal hub 50 which, in this embodiment, is made from plastics. This hub further comprises a fluidic coupler (not shown) for coupling the infusion tubing 10 to the cannula assembly and an electric coupler (not shown) for coupling the pressure sensor 15 to the infusion device 5. At the device-side proximal end 12 of the infusion tubing 10 a fluidic connector (not shown) such as a Luer connector or the like is provided for coupling to the infusion device. The infusion cannula 20 projects out of the hub 50 and may be made of a polymeric material, such as Teflon, or metal, such as medical grade stainless steel. The hub 50 is attached to the patient's skin with its skin-contacting surface 52 via a skin compatible adhesive layer. The pressure sensor 15 may be designed in accordance with any embodiment described herein.

Figure 1:
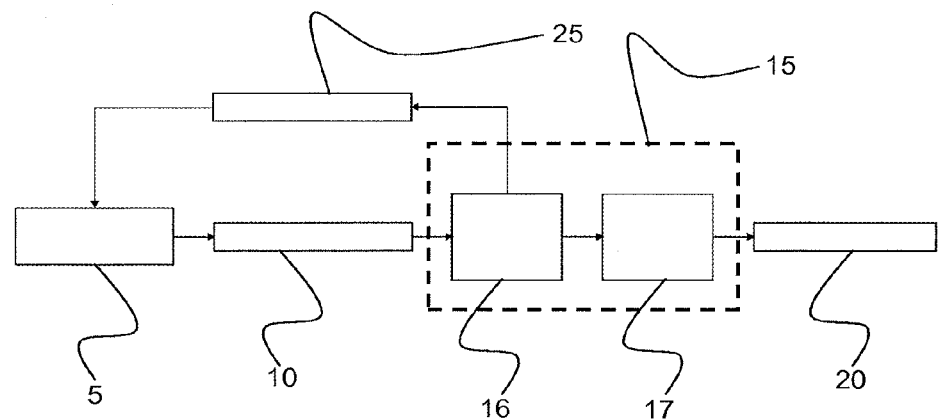
FIG. 1 schematically depicts the overall architecture of an ambulatory infusion system according to one or more embodiments shown and described herein.
Figure 4:
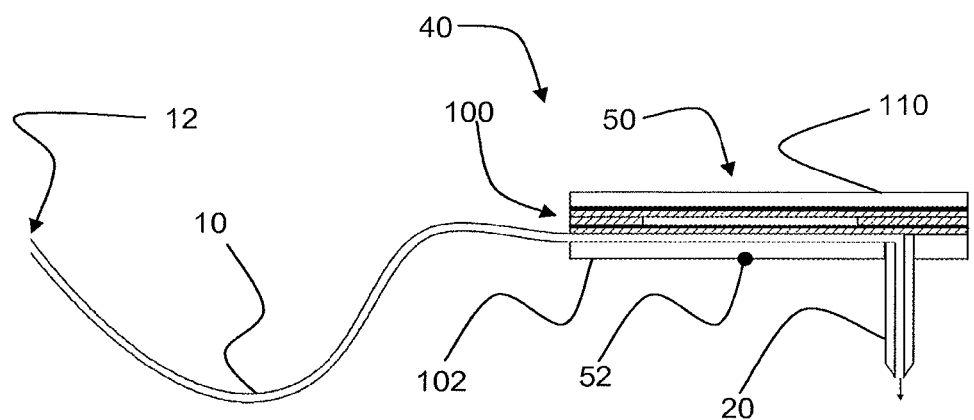

Referring to FIG. 1 and FIG. 4, another embodiment of a cannula assembly 40 is schematically depicted. The pressure sensor 15 is realized as a stack 100 of coplanar layers. The base layer 102 and the top layer 110 are integral with the rigid structure of the hub 50. Exemplary designs of the pressure sensor 15 and in particular of the stack 100 are described in more detail herein.

The measuring unit 25 depicted in FIG. 1 may be integrated into the infusion device 5 or may be fully or partially integrated into the hub 50 of the cannula assembly 40 and in close proximity to the pressure sensor 15. In particular, the capacitance measurement circuitry is advantageously located close to the pressure sensor 15 in order to minimize signal distortions of the low-energy measurement signal and in order to minimize or fully avoid undesired wiring capacitances in parallel with the sensing capacitor. Additional components of the measuring unit 25, such as an analog-to-digital converter for converting the measurement signal, may be provided in the hub 50. In some designs, all components of the measuring unit 25, including the circuitry for evaluating the signals generated by the pressure sensor 15, are located in the hub 50.

Those components of the measuring unit 25 which are included in the hub 50 are designed for single-use and are disposed of as part of the cannula assembly after some days of use. The measuring unit 25 may alternatively be fully or partially incorporated in a separate housing which is configured to be removably attached to the hub 50. This embodiment allows re-use of the measuring unit 25 while still allowing it to be located in close proximity to the pressure sensor 15.

FIG. 5 schematically depicts a stack 100 of coplanar layers of an exemplary pressure sensor 15 in cross-section. As with the preceding and following figures, the dimensions of the figures are not to scale. The layers of the stack 100 are arranged in a sandwich-like manner. The stack 100 comprises a substantially rigid base layer 102 and top layer 110 between which the other layers are arranged. The electrode layer 106 and the counter-electrode layer 108 of the sensing capacitor 300 are separated by an electrode first spacer layer 109 which defines the distance between the electrode and the counter-electrode. A fluid channel 115 for conducting the drug from a drug inlet 114 to the drug outlet 116 is defined by the base layer 102 and an electrode sealing layer 104, the electrode sealing layer 104 separating the fluid channel 115 from the electrode layer 106. The electrode first spacer layer 109 comprises a through cut-out which forms the electrode cavity 112. The through cut-out and, thus, the electrode cavity 112 may be circular, elliptical, substantially rectangular or any other suitable geometrical configuration. The combination of the electrode layer 106 and the electrode sealing layer 104 is resilient such that they flex perpendicular to the flow direction F into the electrode cavity 112. The fluid channel 115 is widened in the area of the electrode cavity 112 to a fluid cavity (not shown) of the same size and in alignment with the electrode cavity.

The electrode cavity 112 may be completely encapsulated such that the fluidic drug pressure is measured with respect to a constant reference pressure inside the electrode cavity 112. Alternatively, the electrode cavity 112 may be vented to the environment by a venting aperture (not shown), such that 'positive pressure' and 'negative pressure' are defined with respect to the environmental air pressure at any point in time.

The electrode first spacer layer 109 is made from a foil which is connected with the electrode layer 106 and the counter-electrode layer 108 by bonding or laminating. The base layer 102 and the top layer 110 are made from rigid plastics and may be part of the hub housing.

In combination, the electrode layer 106 and the counter-electrode layer 108 form the electrodes of a sensing capacitor 300 the dielectric constant of which is largely given by the air or gas inside the electrode cavity 112 with the electrode distance being defined by the thickness of the electrode first spacer layer 109. In addition, there is a parallel offset capacitor. The offset capacitor is defined by the surface of the electrode layer 106 and the counter-electrode layer 108 outside the electrode cavity 112 with the electrode first spacer layer 109 serving as a dielectric. A further component of the offset capacitor is defined by the wiring coupling the electrode layer 106 and the counter electrode layer 108 to the measuring unit 25. In order to minimize the undesired capacitance offset of the sensing capacitor, the surface of the electrode layer 106 and the counter-electrode layer 108 outside the electrode cavity 112 should be kept as small as possible and the wiring for electrically connecting the electrode layer 106 and the counter-electrode layer 108 should be as short as possible.

In the area of the electrode cavity 112, the width of the fluid channel increases to form a fluid cavity such that the fluidic pressure of the drug inside the fluid channel 115 acts on the whole surface area of the electrode layer 106 in the area of the electrode cavity 112.

For a positive pressure of the drug in the fluid channel 115, the electrode sealing layer 104 and the electrode layer 106 will flex into the sensing electrode cavity 112, thus reducing the distance between the electrode layer 106 and the counter-electrode layer 108 and increasing the capacitance of the sensing capacitor. Conversely, a negative pressure of the drug in the fluid channel 115 results the electrode sealing layer 104 and the electrode layer 106 to flex into the fluid channel 115, thus increasing the distance between the electrode layer 106 and the counter-electrode layer 108 and reducing the capacitance of the sensing capacitor. The electrode layer and the counter-electrode layer are electrically coupled to the measuring unit 25 which is schematically represented by an impedance meter.

The rigidity of the electrode layer 106 and the electrode sealing layer 104, as well as the thickness of the electrode first spacer layer 109 may be selected such that the electrode layer and the counter-electrode layer do not come into contact at the highest fluidic pressure in the fluid channel 115 which may occur, for example, in case of an occlusion. In this case, the capacitance measurement circuit is designed for capacitance measurement only. However, the rigidity of the electrode layer 106 and the electrode sealing layer 104 may alternatively be such that, upon a given threshold maximum pressure, the electrode layer 106 touches the counter-electrode layer 108, thus establishing a galvanic contact. This galvanic contact may additionally be detected by the capacitance measurement circuit of the measuring unit 25 or by a controller of the infusion device.

While several modifications and variations are disclosed and discussed in further exemplary embodiments below, the principle design is the same and follows the description as given with reference to FIG. 5.

Figure 6:
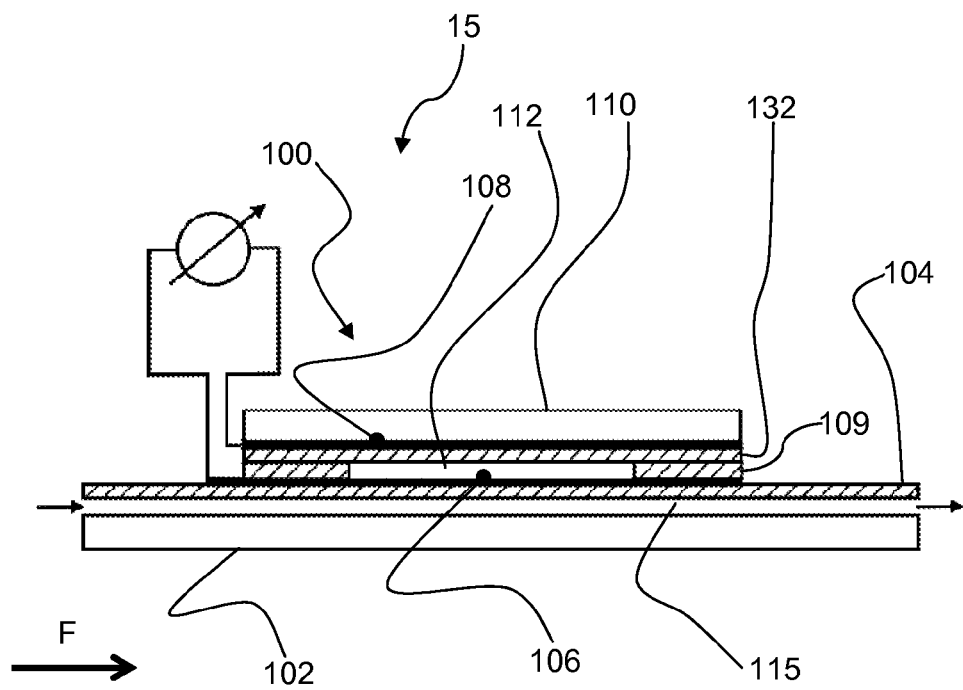

FIG. 6 depicts a stack 100 of coplanar layers of another embodiment of a pressure sensor 15. In the embodiment shown in FIG. 6, the counter-electrode layer 108 comprises an insulation layer which faces the electrode layer 106. The insulation layer 132 prevents the electrode layer 106 and the counter-electrode layer 108 from establishing a galvanic contact. Instead, when the electrode layer 106 contacts the insulation layer 132, the capacitance of the sensing capacitor shows saturation. Additionally or alternatively to the insulation layer 132, an insulation layer may be positioned on the electrode layer 106.

Figure 7:
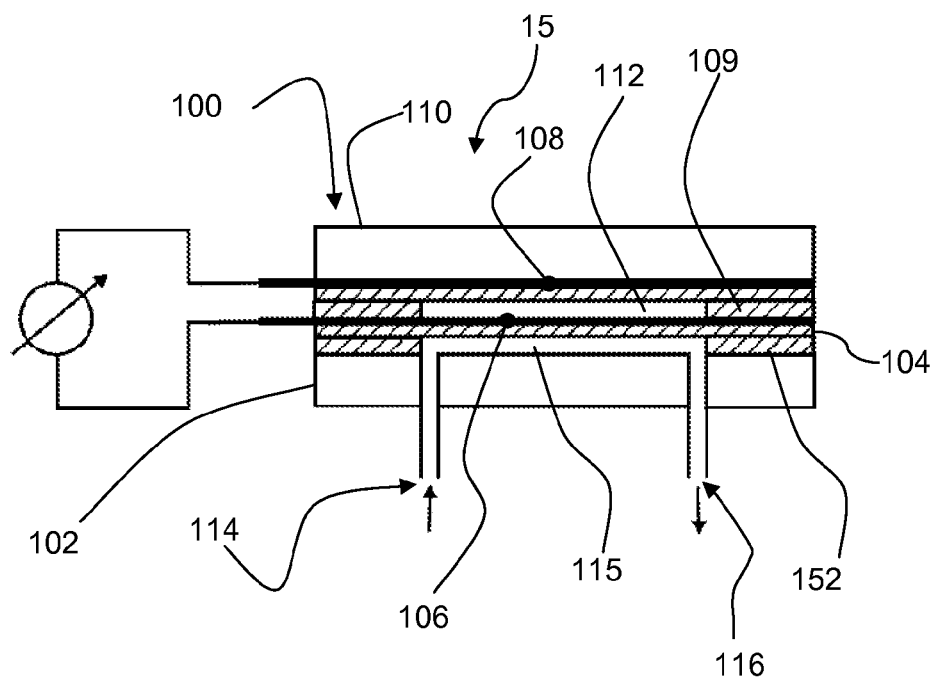

FIG. 7 schematically depicts another embodiment of a stack 100 of coplanar layers of an exemplary pressure sensor 15. In this embodiment the drug inlet 114 and the drug outlet 116 are perpendicular to the flow direction F of the drug inside the sensor. For the drug inlet 114 and the drug outlet 116, bores (not referenced) are provided in the base layer 102. A fluid channel spacer layer 152 is provided between the base layer 102 and the electrode sealing layer 104. The base layer 102, the fluid channel spacer layer 152, and the electrode sealing layer 104, in combination, define the fluid channel 115.

Alternatively, instead of providing a dedicated fluid channel spacer layer 152, the fluid channel 115 may be formed by structuring the base layer 102 as described above.

In another embodiment (not shown), one of the drug inlet 114 or the drug outlet 116 is tangential or perpendicular with the stacked layers and the flow direction F, while the other of the drug inlet 114 or the drug outlet 116 is perpendicular to the stacked layers. An embodiment having this configuration is depicted in FIG. 4 where the drug outlet 116 may be perpendicular to the stacked layers for cannula assembly designs when the cannula is placed into the patient's subcutaneous tissue substantially perpendicular to the skin. In contrast, a design with the drug outlet 116 tangential with the stacked layers may be advantageous for a design of the cannula assembly where the infusion cannula is placed into the patients skin with a small angle of, for example, 10° to 20°.

Figure 8A:
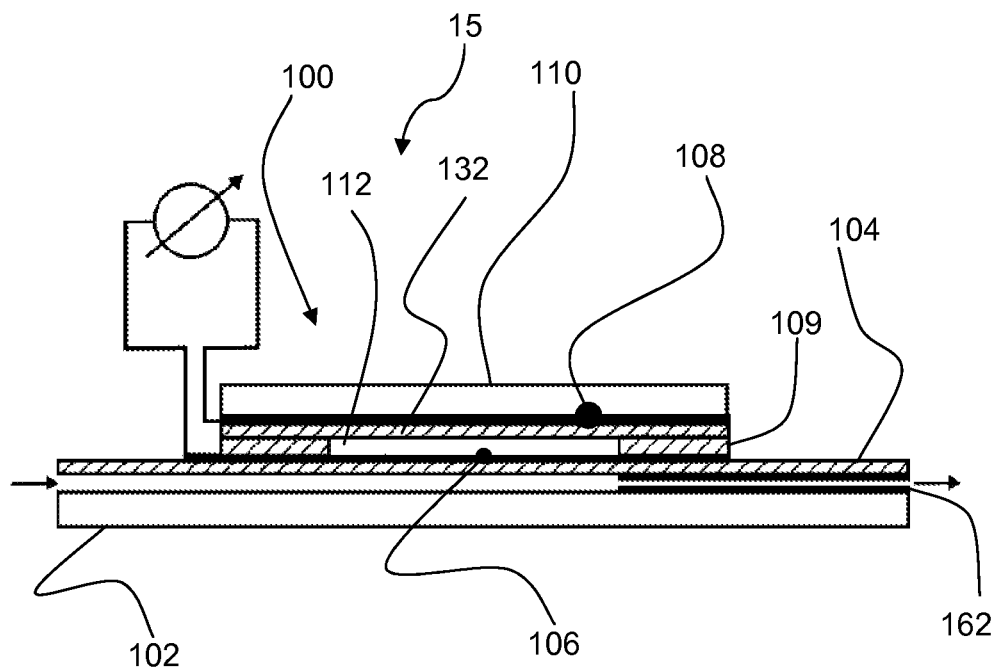
FIG. 8a schematically depicts a stack of coplanar layers of another exemplary pressure sensor according to one or more embodiments shown and described herein.

FIG. 8*a* schematically depicts another embodiment of a pressure sensor 15 comprising a stack 100 of coplanar layers. The pressure sensor is designed similar to the pressure sensor shown in FIG. 5 and described above, but further comprises a flow restrictor 162 which provides additional fluidic resistance downstream of the sensing capacitor, thus improving the pressure change that can be measured by the pressure sensor during drug administration.

Figure 8B:
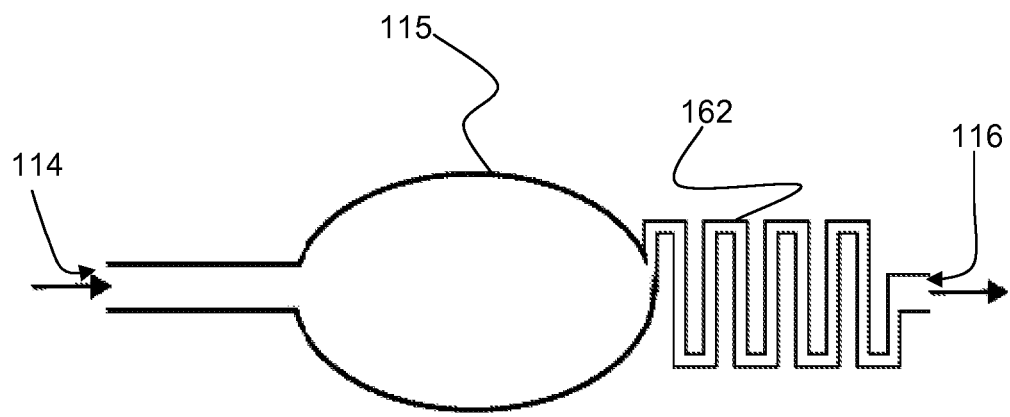

FIG. 8*b* schematically shows the fluidic arrangement according to FIG. 8*a* from a top-view or bottom view. The fluid channel 115 is widened to form an elliptical fluid cavity corresponding to the shape of the electrode cavity 112 in the area of the sensing capacitor. The flow restrictor 162 is arranged downstream of the electrode cavity and is serpentine shaped. This shape is favorable for the flow restrictor 162 since it creates a long fluid path with a short distance in the flow direction F, thus enabling a compact design. However, other alternative shapes may be used as well.

The fluid channel 115, including the serpentine flow-restrictor 162, may be formed by structuring the base layer 102. Alternatively, an additional layer (not visible), such as a foil layer, may be provided between the base layer 102 and the electrode sealing layer 104. This additional layer may include a serpentine shape through cut-out or punching which forms the side walls of the fluid channel 115 in the area of the flow restrictor 162.

Figure 9:
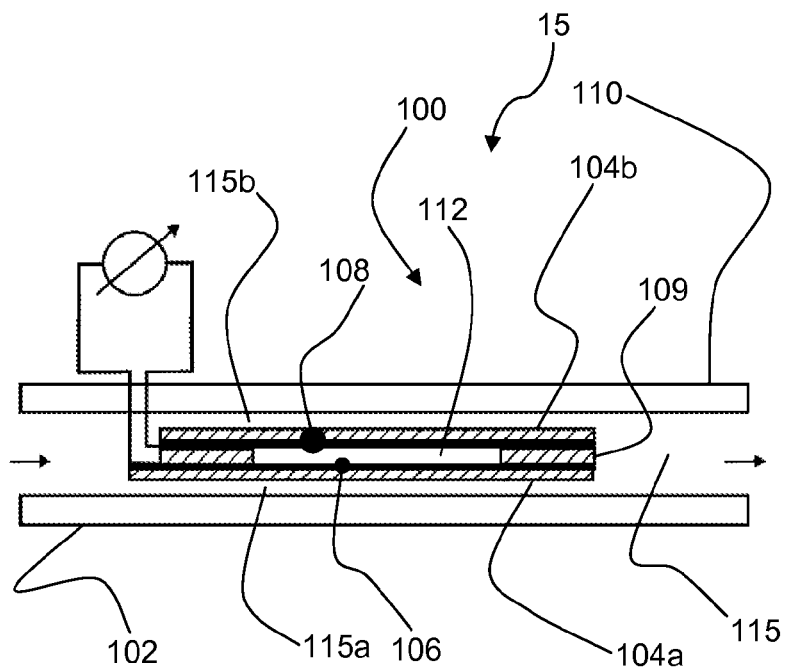
FIG. 9 and FIG. 10 schematically depict stacks of coplanar layers of further exemplary pressure sensors according to one or more embodiments shown and described herein.

FIG. 9 schematically depicts another embodiment of a pressure sensor 15 comprising a stack 100 of coplanar layers. This embodiment is similar to the embodiment of the pressure sensor depicted in FIG. 4 and described above. However, in this embodiment the fluid channel is bifurcated into a first sub-channel 115*a* and a second sub-channel 115*b*. The sensing capacitor is arranged in the fluid channel between the first sub-channel 115*a* and the second sub-channel 115*b* such that the fluidic pressure in the fluid channel 115 acts on both the electrode layer 106 and the counter-electrode layer 108. In this embodiment, both the electrode layer 106 and the counter-electrode layer 108 are flexible under the influence of the fluidic pressure in the fluid channel 115, wherein a positive pressure results in the electrode layer 106 and the counter-electrode layer 108 flexing towards each other. Enabling both the electrode layer 106 and the counter-electrode layer 108 to flex under the influence of the fluidic pressure significantly increases the sensitivity of the pressure sensor.

In this embodiment, the drug in the fluid channel 115 is separated from the counter-electrode layer 108 with a counter-electrode sealing layer 104*b*. While not visible in FIG. 8, the base layer 102 and the electrode sealing layer 104*a* as well as the top layer 110 and the counter-electrode sealing layer 104*b* are spaced by fluid channel spacer layers, such that the fluid channel 115 is divided into the first sub-channel 115*a* between the base layer 102 and the electrode sealing layer 104*a*, and into a second sub-channel 115*b* between the top layer 110 and the counter-electrode-sealing layer 104*b*. Alternatively, the base layer 102 and the top layer 110 may be part of a solid structure, e.g., a housing structure of the hub which supports the inner layers.

The fluidic pressure in the first sub-channel 115*a* acts on the electrode layer 106 and the fluidic pressure in the second sub-channel 115*b* acts on the counter-electrode layer 108 in the area of the electrode cavity 112. The stack 100 may optionally comprise an insulation layer as discussed above with reference to FIG. 6.

Figure 10:
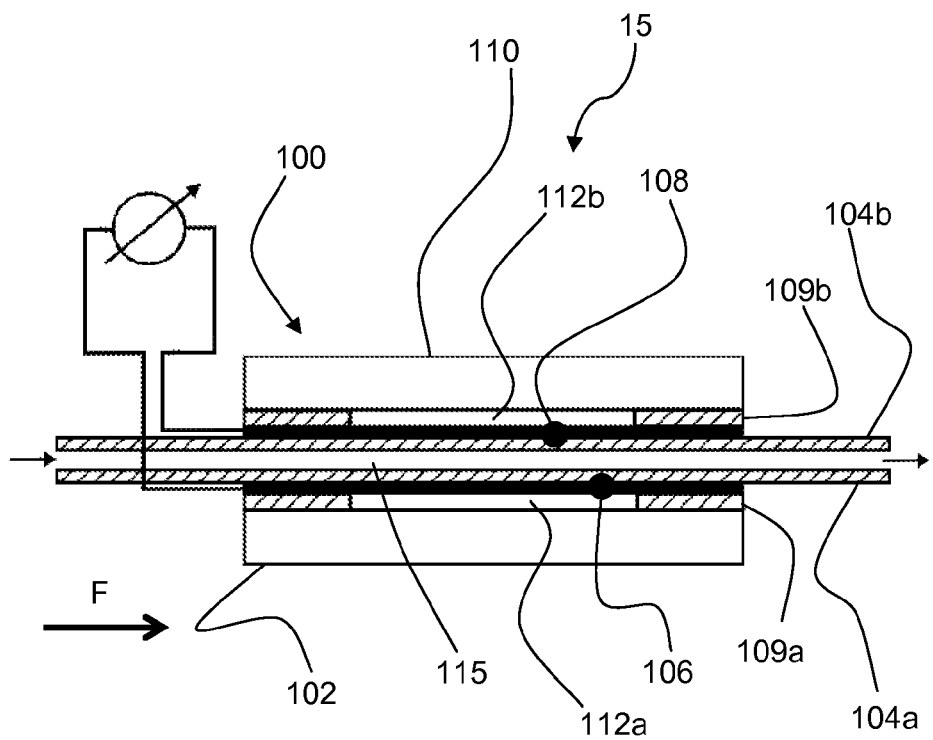

FIG. 10 schematically depicts another embodiment of a pressure sensor 15 comprising a stack 100 of coplanar layers. In this embodiment both the electrode layer 106 as well as the counter-electrode layer 108 are flexible. Here, the fluid channel 115 is arranged between the electrode layer 106 and the counter-electrode layer 108. In this embodiment, a positive pressure in the fluid channel 115 results in the electrode layer 106 and the counter-electrode layer 108 flexing away from each other, thus increasing the electrode distance. The electrode layer 106 is separated from the base layer 102 by the first spacer layer 109a and the counter-electrode layer 108 is separated from the top layer 110 by the second spacer layer 109b. The first spacer layer 109a comprises an electrode cavity 112a into which the electrode layer 106 may flex and the second spacer layer 109b comprises a counter-electrode cavity 112b into which the counter-electrode layer 108 may flex under the influence of a positive fluidic pressure in the fluid channel 115.

Since for this type of embodiment the fluid channel 115 is arranged between the electrode layer 106 and the counter-electrode layer 108, respectively, the dielectric properties of the electrode sealing layer 104a and the counter-electrode sealing layer 104b, respectively, as well as the dielectric properties of the drug in the fluid channel 115 influence the capacitance of the sensing capacitor.

Figure 11:
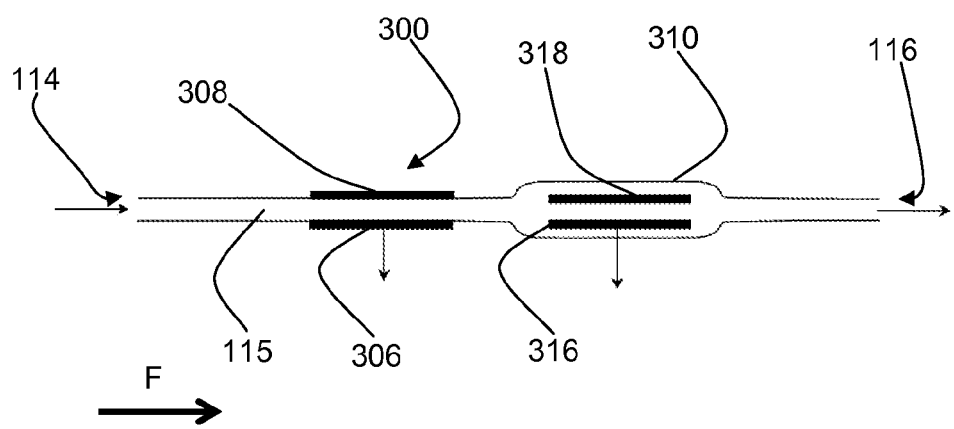
FIG. 11 schematically depicts a pressure sensor in accordance with one or more embodiments shown and described herein.

FIG. 11 schematically depicts another embodiment of a pressure sensor. The pressure sensor comprises a sensing capacitor 300 and a secondary sensing capacitor 310. The sensing capacitor 300 and the secondary sensing capacitor 310 are fluidically arranged in series in the fluid channel between the drug inlet 114 and the drug outlet 116. The sensing capacitor 300 comprises an electrode layer 306 and a counter-electrode layer 308. The secondary sensing capacitor 310 comprises a secondary electrode layer 316 and a secondary counter-electrode layer 318. The secondary sensing capacitor 310 is designed such that a positive fluidic pressure in the fluid channel 115 results in the secondary electrode layer 316 and the secondary counter-electrode layer 318 flexing towards each other, thus decreasing the corresponding electrode distance and increasing the capacitance of the sensing capacitor. The sensing capacitor 300 is flexible such that a positive fluidic pressure in the fluid channel 115 results in the electrode layer 306 and the counter-electrode layer 308 flexing away from each other, thus increasing the corresponding electrode distance and increasing the capacitance of the sensing capacitor. The sensing capacitor 300 may be constructed according to FIG. 10 while the secondary sensing capacitor 310 may be constructed according to FIG. 9. It should be understood that the position of the sensing capacitor 300 and the secondary sensing capacitor 310 may be interchanged. While the sensing capacitor 300 and the secondary sensing capacitor 310 are in series with each other with respect to the flow direction F, they may alternatively be arranged in a stacked configuration to conserve space. Alternatively to being arranged in series, the sensing capacitor 300 and the secondary sensing capacitor 310 may be in a parallel fluidic arrangement.

Figure 12A:
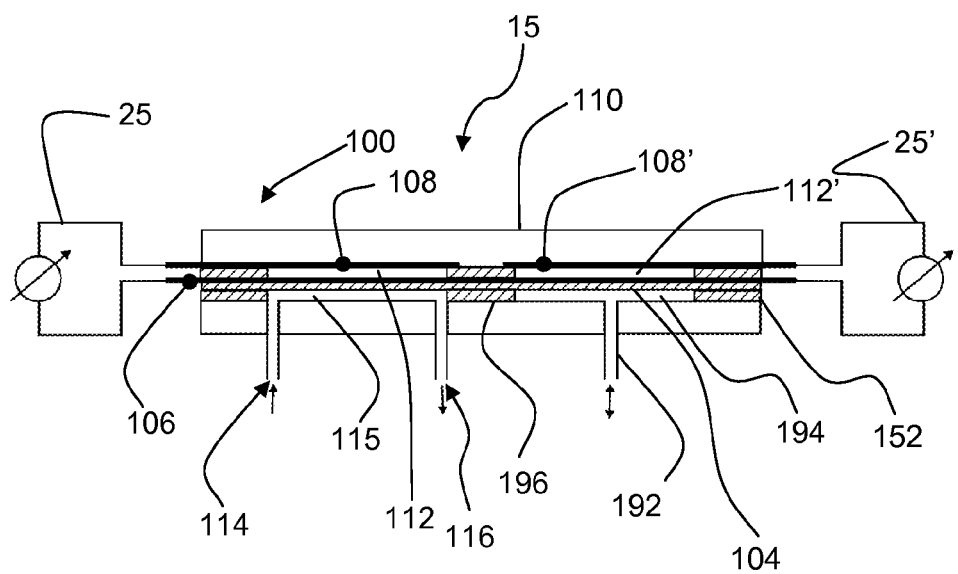
FIG. 12a schematically depicts a stack of coplanar layers of a further exemplary pressure sensor according to one or more embodiments shown and described herein.

FIG. 12a schematically depicts another embodiment of a pressure sensor 15 comprising a stack 100 of coplanar layers. The sensing capacitor of this embodiment is constructed in a similar manner as the sensing capacitor shown in FIG. 5 with the drug inlet 114 and the drug outlet 116 arranged as depicted in FIG. 7. In addition, the stack 100 includes a reference capacitor.

For this purpose, the stack is enlarged such that the electrode layer 106 covers a reference pressure cavity 194 which is vented to the environment via a reference venting aperture 192. The reference pressure cavity 194 is analogous to the fluid cavity of the fluid channel 115 for the sensing capacitor. A reference electrode cavity 112' as well as a reference counter-electrode layer 108' are arranged in an analogous way to the electrode cavity 112 and the counter-electrode layer 108. The two capacitors are separated by a separation area 196 in which the sandwich of the electrode layer 106 and the electrode sealing layer 104 is fixed to the fluid channel spacer layer 152. Accordingly, the electrode layer 106 may flex into the electrode cavity 112 under the influence of the fluidic pressure in the fluid channel 115 and may independently flex into the reference electrode cavity 112' under the influence of a positive air pressure in the reference pressure cavity 194. Similarly, the electrode layer 106 may flex into the fluid channel 115 and may independently flex into the reference pressure cavity 194 under the influence of a negative pressure in the fluid channel 115 or the reference pressure cavity 194, respectively.

Figure 12B:
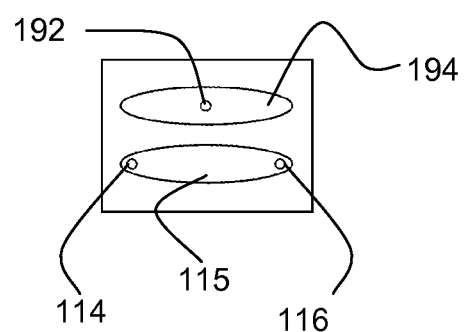

FIG. 12b schematically depicts a bottom view of the pressure sensor of FIG. 12a. The fluid channel 115 is widened to an elliptical fluid cavity in the area of the sensing capacitor with the drug inlet 114 and the drug outlet 116 being arranged at opposed ends of the major axis of the ellipse. The reference pressure cavity 194 is of the same design and size as the central reference venting aperture 192 being arranged in the center of the ellipse. The reference venting aperture 192 may be sealed with a membrane (not shown) which is air permeable but prevents dust and humidity from entering the reference pressure cavity 194. Due to the symmetric design of the sensing capacitor and the reference capacitor, the nominal capacitances of both capacitors are identical besides tolerances. However, the nominal capacitances may alternatively be different by design.

Alternative to the side-by-side design shown in FIG. 12a and FIG. 12b, the sensing capacitor and the reference capacitor may be arranged in a stacked arrangement with one of the capacitors arranged on top of the other capacitor.

The capacitance of the reference capacitor is measured by a reference capacitance measuring unit 25' which may be integral with the measuring unit 25.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:
1. An ambulatory infusion system for the infusion of a liquid drug into a patient's body over an extended time period, the ambulatory infusion system comprising:
   an infusion device an infusion cannula fluidically coupled to the infusion device;
   a measuring unit;
   a pressure sensor electrically coupled to the measuring unit and fluidically coupled to the infusion cannula with a fluid channel, the pressure sensor comprising a stack of coplanar layers comprising:
   a rigid top layer and a rigid base layer, wherein at least a portion of the fluid channel is positioned between the top layer and the base layer;
   an electrode layer positioned between the top layer and the base layer and flexibly coupled to the fluid channel;
   a counter-electrode layer positioned between the top layer and the electrode layer, the counter-electrode layer and the electrode layer forming electrodes of a sensing capacitor; and
   a spacer layer defining an electrode cavity disposed between the top layer and the base layer such that the electrode layer extends across the electrode cavity, wherein positive fluidic pressure in the fluid channel flexes the electrode layer into the electrode cavity thereby modifying a capacitance of the sensing capacitor; and wherein the electrode layer and the spacer layer that are arranged between the top layer and the bottom layer are of substantially the same size.

2. The ambulatory infusion system according to claim 1, wherein the pressure sensor further comprises a reference capacitor comprising the electrode layer and a reference counter-electrode layer.

3. The ambulatory infusion system of claim 1 further comprising a reference pressure cavity disposed between the electrode layer and the base layer.

4. The ambulatory infusion system of claim 3 wherein the electrode layer can flex into the electrode cavity under the influence of fluidic pressure in the fluid channel.

5. The ambulatory infusion system of claim 3 wherein the electrode layer flexes into the fluid channel and independently flexes into the reference pressure cavity under the influence of a negative pressure in the fluid channel or the reference pressure cavity, respectively.

6. The ambulatory infusion system of claim 3 wherein the reference pressure cavity and the fluid channel are separated by a separation area.

7. The ambulatory infusion system of claim 1 wherein the reference pressure cavity is vented to the environment via a reference venting aperture extending through the base layer.

8. The ambulatory infusion system of claim 1 further comprising a reference capacitance measuring unit coupled to the electrode layer and the counter electrode layer.

9. The ambulatory infusion system of claim 1 further comprising an electrode sealing layer disposed between the electrode layer and the reference pressure cavity.

10. The ambulatory infusion system of claim 9 wherein the electrode sealing layer is resilient in order to allow it to flex together with the electrode layer.

11. The ambulatory infusion system of claim 1 wherein he electrode layer and the spacer layer are made from foils.

12. An ambulatory infusion system for the infusion of a liquid drug into a patient's body over an extended time period, the ambulatory infusion system comprising:
  an infusion cannula fluidically coupled to the infusion device;
  a measuring unit;
  a pressure sensor electrically coupled to the measuring unit and fluidically coupled to the infusion cannula with a fluid channel, the pressure sensor comprising a stack of coplanar layers comprising:
    a rigid top layer and a rigid base layer, wherein at least a portion of the fluid channel is positioned between the top layer and the base layer;
    an electrode layer positioned between the top layer and the base layer and flexibly coupled to the fluid channel;
    a counter-electrode layer positioned between the top layer and the electrode layer, the counter-electrode layer and the electrode layer forming electrodes of a sensing capacitor; and
    a spacer layer defining an electrode cavity disposed between the top layer and the base layer such that the electrode layer extends across the electrode cavity, wherein positive fluidic pressure in the fluid channel flexes the electrode layer into the electrode cavity thereby modifying a capacitance of the sensing capacitor; and wherein the electrode layer and the spacer layer are substantially the same length prior to a cut-out which forms the electrode cavity.

* * * * *